(12) United States Patent
Bower et al.

(10) Patent No.: US 8,896,842 B2
(45) Date of Patent: Nov. 25, 2014

(54) COMPACT MULTIMODALITY OPTICAL COHERENCE TOMOGRAPHY IMAGING SYSTEMS

(75) Inventors: Bradley A. Bower, Hillsborough, NC (US); Robert H. Hart, Cary, NC (US); Pete Huening, Clayton, NC (US); Eric L. Buckland, Hickory, NC (US)

(73) Assignee: Bioptigen, Inc., Durham, NC (US)

( * ) Notice: Subject to any disclaimer, the term of this patent is extended or adjusted under 35 U.S.C. 154(b) by 536 days.

(21) Appl. No.: 13/198,117

(22) Filed: Aug. 4, 2011

(65) Prior Publication Data
US 2012/0033227 A1 Feb. 9, 2012

Related U.S. Application Data

(60) Provisional application No. 61/370,993, filed on Aug. 5, 2010, provisional application No. 61/412,558, filed on Nov. 11, 2010.

(51) Int. Cl.
| | | |
|---|---|---|
| G01B 9/02 | (2006.01) | |
| A61B 3/10 | (2006.01) | |
| A61B 3/14 | (2006.01) | |

(52) U.S. Cl.
CPC .. *A61B 3/102* (2013.01); *A61B 3/14* (2013.01)
USPC ...................................................... 356/497

(58) Field of Classification Search
CPC ... A61B 3/102; A61B 5/0066; G01B 9/02091
USPC ................................................. 356/479, 497
See application file for complete search history.

(56) References Cited

U.S. PATENT DOCUMENTS

| | | |
|---|---|---|
| 5,455,644 A | 10/1995 | Yazawa et al. |
| 5,506,634 A | 4/1996 | Wei et al. |

(Continued)

FOREIGN PATENT DOCUMENTS

| | | |
|---|---|---|
| WO | WO 00/04820 A1 | 2/2000 |

OTHER PUBLICATIONS

Framme et al., "Noninvasive Imaging and Monitoring of Retinal Pigment Epithelium Patterns Using Fundus Autofluorescence—Review," *Current Medical Imaging Reviews*, 2005, 1, pp. 89-103.

(Continued)

*Primary Examiner* — Hwa Lee
(74) *Attorney, Agent, or Firm* — Myers Bigel Sibley & Sajovec

(57) ABSTRACT

Systems for imaging a sample are provided. The system includes an optical coherence tomography (OCT) imaging portion having an associated OCT path defined by one set of optical elements between an OCT signal delivery optical fiber and the sample; an image capture portion having an associated image capture path defined by a second set of optical elements between an image capture device and the sample, different from the OCT path; and an illuminator portion having an associated illumination path defined by a third set of optical elements between an illumination source and the sample. The OCT path, the image capture path, and the illuminator path have at least one optical element in common, and the respective paths differ from each other by at least one optical element. The OCT path and the image capture path share a common intermediate conjugate image plane. Focal control is achieved for the OCT path and the image capture path concurrently through adjustment of one or more common optical elements distal to the common intermediate conjugate plane, such that focal control requires no differential adjustment between optical elements not in common to both paths.

12 Claims, 13 Drawing Sheets

(56) References Cited

U.S. PATENT DOCUMENTS

| | | | |
|---|---|---|---|
| 5,822,036 | A | 10/1998 | Massie et al. |
| 6,006,128 | A | 12/1999 | Izatt et al. |
| 6,741,359 | B2 | 5/2004 | Wei et al. |
| 7,123,751 | B1 | 10/2006 | Fujieda |
| 7,140,730 | B2 | 11/2006 | Wei et al. |
| 7,400,410 | B2 | 7/2008 | Baker et al. |
| 7,614,744 | B2 * | 11/2009 | Abe .............................. 351/209 |
| 7,830,525 | B2 | 11/2010 | Buckland et al. |
| 2007/0081166 | A1 | 4/2007 | Brown et al. |
| 2007/0285618 | A1 | 12/2007 | Chinaglia et al. |
| 2009/0141237 | A1 | 6/2009 | Izatt et al. |
| 2009/0163898 | A1 | 6/2009 | Gertner et al. |
| 2009/0268020 | A1 | 10/2009 | Buckland et al. |
| 2009/0268161 | A1 | 10/2009 | Hart et al. |
| 2010/0053553 | A1 | 3/2010 | Zinser |
| 2010/0315592 | A1 | 12/2010 | Buckland et al. |
| 2010/0321636 | A1 | 12/2010 | Buckland et al. |

OTHER PUBLICATIONS

Kwong et al., "400-Hz mechanical scanning optical delay line," *Optics Letters*, vol. 18, No. 7, Apr. 1, 1993, pp. 558-560.

DeHoog et al., "Fundus camera systems: a comparative analysis," *Applied Optics*, vol. 48, No. 2, Jan. 10, 2009, pp. 221-228.

DeHoog et al., "Optimal parameters for retinal illumination and imaging in fundus cameras," *Applied Optics*, vol. 47, No. 36, Dec. 20, 2008, pp. 6769-6777.

"Economic Costs Associated with Mental Retardation, Cerebral Palsy, Hearing Loss, and Vision Impairment," *Morbidity and Mortality Weekly Report (Centers for Disease Control and Prevention)*, Jan. 30, 2004, vol. 53, No. 3, pp. 57-59.

Stopa et al, "Correlation of Pathologic Features in Spectral Doman Optical Coherence Tomography with Conventional Retinal Studies," *Retina*, vol. 28, 2008, pp. 298-308.

Maldonado et al., "Optimizing Hand-held Spectral Domain Optical Coherence Tomography Imaging for Neonates, Infants, and Children," *Investigative Ophthalmology & Visual Science*, vol. 51, 2010, pp. 2678-2685.

Chavala et al., "Insights into Advanced Retinopathy of Prematurity Using Handheld Spectral Domain Optical Coherence Tomography Imaging," *Ophthalmology*, vol. 116, 2009, pp. 2448-2456.

Scott et al., "Imaging the infant retina with a hand-held spectral-domain optical coherence tomography device," *American Journal of Ophthalmology*, vol. 147, 2009, pp. 364-373.

Tanna et al., "Retinal Imaging Using Commercial Broadband Optical Coherence Tomography," *British Journal of Ophthalmology*, vol. 94, 2009, pp. 372-376.

Rollins et al., "In vivo video rate optical coherence tomography," *Optics Express*, vol. 3, No. 6, Sep. 14, 1998, pp. 219-229.

Pennie et al., "A longitudinal study of the biometric and refractive changes in full-term infants during the first year of life," *Vision Research*, vol. 41, 2001, pp. 2799-2810.

Invitation to Pay Additional Fees Corresponding to International Application No. PCT/US2011/046559; Date of Mailing; Nov. 24, 2011; 5 pages.

International Preliminary Report on Patentability Corresponding to International Application No. PCT/US2011/046559; Date of Mailing: Feb. 14, 2013; 13 Pages.

International Search Report Corresponding to International Application No. PCT/US2011/046559; Date of Mailing: Mar. 13, 2012; 25 pages.

\* cited by examiner

COMPACT MULTIMODALITY OPTICAL COHERENCE TOMOGRAPHY IMAGING SYSTEMS

CLAIM OF PRIORITY

The present application claims priority from U.S. Provisional Application No. 61/370,993, filed Aug. 5, 2010 and U.S. Provisional Application No. 61/412,558, filed Nov. 11, 2010, the disclosures of which are hereby incorporated herein by reference as if set forth in their entirety.

STATEMENT OF GOVERNMENT SUPPORT

This invention was made with government support under grant number 1R43EY01900 awarded by National Institutes of Health, National Eye Institute. The United States Government has certain rights in this invention.

FIELD

The present invention relates to imaging and, more particularly, to optical coherence tomography (OCT) and related systems and methods.

BACKGROUND

Visual field testing is a conventional clinical method utilized in the diagnosis of eye diseases that cause degradation of vision sensitivity. One method utilized in the diagnosis of such diseases is the Standard Automated Perimeter (SAP) test, which tests brightness contrast sensitivity over a large visual field. There are many instruments for performing an SAP test routinely used in clinics including, for example, those produced by Carl Zeiss Meditec (Dublin, Calif.).

Typically, visual field testing utilizes functional field testing techniques. However, a functional field test technique is a functional test of vision degradation. Due to the human eye's complex multiplexing capability, the functional field test is not a sensitive measure of eye structure, which would be highly useful in the early diagnoses of such eye diseases before substantial degradation has occurred. Such structural tests include, for example, retinal image testing and optical coherence tomography (OCT).

Retinal image testing can be performed with conventional optical imaging methodology and has been routinely used in clinics for retinal structure change evaluation in addition to visual field tests. Devices such as a fundus camera, a scanning laser ophthalmoscope (SLO) or an indirect ophthalmoscope are routinely used for such testing. The retinal image provides valuable information that clinicians can utilize to diagnosis eye diseases. However, only qualitative interpretation of eye structure changes from the retinal photographs can be observed by highly experienced clinicians.

Accordingly, OCT has been used for non-invasive human eye retinal imaging. The cross sectional retinal image provided by an OCT system may allow a clinician to quantitatively evaluate the retinal nerve layer and retinal thickness. Thus, the OCT system may provide valuable clinical information that can be used for early diagnosis of eye diseases, such as Age-Related Macular Degeneration, Diabetic Retinopathy and Glaucoma.

OCT has been adopted as a standard of care for structural imaging of the eye for retinal and anterior structures. Video fundus photography and scanning laser ophthalmoscopy remain important modalities for capturing high resolution, high contrast en face photographs. Additionally, these modalities are useful for color photography and fluorescent imaging that provide complementary signatures of disease.

To date, OCT imaging systems have been largely bulky tabletop systems appropriate to clinical imaging of ambulatory patients. Handheld OCT produced by Bioptigen is the first compact system for ophthalmic imaging of pediatric, confined, or infirm patients that does not require the patient to sit a tabletop instrument as discussed in commonly assigned United States Patent Publication No. 2009/0268020.

The details of OCT systems used for imaging the human eye are discussed in, for example, U.S. Pat. No. 7,140,730 to Jay Wei et al. entitled *Optical Apparatus and Method for Comprehensive Eye Diagnosis*, the disclosure of which is hereby incorporated herein by reference as if set forth in its entirety. OCT scanners used for imaging the human eye are discussed, for example, in U.S. Pat. No. 6,741,359 to Jay Wei et al. entitled *Optical Coherence Tomography Optical Scanner*, the disclosure of which is hereby incorporated herein by reference as if set forth in its entirety.

Further discussion of OCT and related systems, methods and computer program product can be found in commonly assigned U.S. Pat. No. 7,830,525 and United States Patent Publication Nos. 2007/0081166; 2010/0315592; 2010/0321636; 2009/0141237 and 2009/0268161, the disclosures of which are hereby incorporated herein by reference as if set forth in their entirety.

SUMMARY

Some embodiments of the present inventive concept provide systems for imaging a sample. The system includes an optical coherence tomography (OCT) imaging portion having an associated OCT path defined by one set of optical elements between an OCT signal delivery optical fiber and the sample; an image capture portion having an associated image capture path defined by a second set of optical elements between an image capture device and the sample, different from the OCT path; and an illuminator portion having an associated illumination path defined by a third set of optical elements between an illumination source and the sample. The OCT path, the image capture path, and the illuminator path have at least one optical element in common, and the respective paths differ from each other by at least one optical element. The OCT path and the image capture path share a common intermediate conjugate image plane. Focal control is achieved for the OCT path and the image capture path concurrently through adjustment of one or more common optical elements distal to the common intermediate conjugate plane, such that focal control requires no differential adjustment between optical elements not in common to both paths.

In further embodiments, the illuminator may include a compact wide field on-axis illuminator without a path element or an optical stop that interferes with the OCT path.

In still further embodiments, the illuminator may include a fiber ring illuminator. In certain embodiments, the fiber ring illuminator may include a ring of optical fibers that defines an annulus, the annulus having an inner diameter, an outer diameter and a radiant numerical aperture, the radiant numerical aperture being approximately 0.22 and between 0.16 and 0.28.

In some embodiments, the system further includes a collimating lens following the fiber ring illuminator. An image of the ring illuminator may be focused onto the vicinity of a pupil of an eye of a subject such that the outer diameter of the annulus imaged onto the pupil is less than a diameter of the pupil. The inner diameter of the annulus at the pupil plane may be less than a pupil diameter.

In further embodiments, the illumination portion may include a fixation target. In certain embodiments, the fixation target may include one or more single-mode optical fibers, the output of the single mode optical fibers displaced with respect to the output of the illuminator, such that the one or more single mode fibers is conjugate to the intermediate conjugate image plane of the OCT path.

In still further embodiments, the image capture portion may be further configured to provide a real-time video image to aid alignment of an OCT beam; capture a photographic reference image of a sample to use as a comparison to an OCT depth-resolved image; enable full color or hyperspectral photography for emphasizing various features of an imaged structure and various depths of the image structure; and/or enable fluorescent image photography for emphasizing various features of the imaged structure and various depths of the image structure.

In still further embodiments, hyperspectral images provide additional clinical diagnostic value when correlated to depth resolved structural OCT images.

In some embodiments, the illumination/fixation path includes a light source having a range of from about 650 to about 740 nm. In certain embodiments, the light source comprises a light emitting diode (LED).

In further embodiments, the OCT path may be coupled to the image capture path though a polarization independent dichroic beamsplitter. The dichrotic beamsplitter may be a thin film filter.

In still further embodiments, the system further includes a real-time range finder configured to guide a photographer to a correct working distance, the working distance being relative to a subject's cornea.

In some embodiments, the system further includes an electromechanical reference arm.

In further embodiments, the system is fitted within a compact housing, the housing including a cable tether to remainder of the OCT system, the housing sized to provide a handheld system for imaging a sample.

Still further embodiments provide methods for imaging a sample in an optical coherence tomography system, the OCT system including an OCT portion having an associated OCT path, an image capture portion having an associated image capture path, different from the OCT path and an illuminator with an optional fixation target having an associated illumination/fixation path, different from the OCT path and the image capture path. The method includes operating in an OCT only examination mode; operating in an image capture only mode; operating in a combined operation mode; or operating in a short duration flash operation mode.

In some embodiments, operating the system in an image capture only mode includes lowering the optical power of an OCT signal of the system; and increasing the optical power radiating from a ring illumination source. The combined optical powers irradiating a subject across the imaging sequence remains below a maximum permissible exposure level.

In further embodiments, operating the system in the short duration flash operation mode includes operating at an elevated power level for a brief time period to acquire a snapshot, the elevated power level illuminating the subject at between 2 and 10 mW/cm$^2$.

In still further embodiments, an imaging cycle of the OCT system may include operating in an image capture mode for exploratory examination of a fundus with the OCT mode off in order to identify a region of interest; operating in a combined operation mode, wherein the OCT mode is operating in a two-orthogonal-axis aiming mode and the image capture mode is operating in low power mode as an alignment support device to locate an OCT beam on a region of interest such that the combined exposure remains below a maximum permissible exposure level; operating in a short duration flash operation mode for a flash short duration high intensity image acquisition with an image capture device, the OCT mode being off; and acquiring an OCT image sequence with low level video illumination and digital image capture on or off.

DETAILED DESCRIPTION

Figure 1:
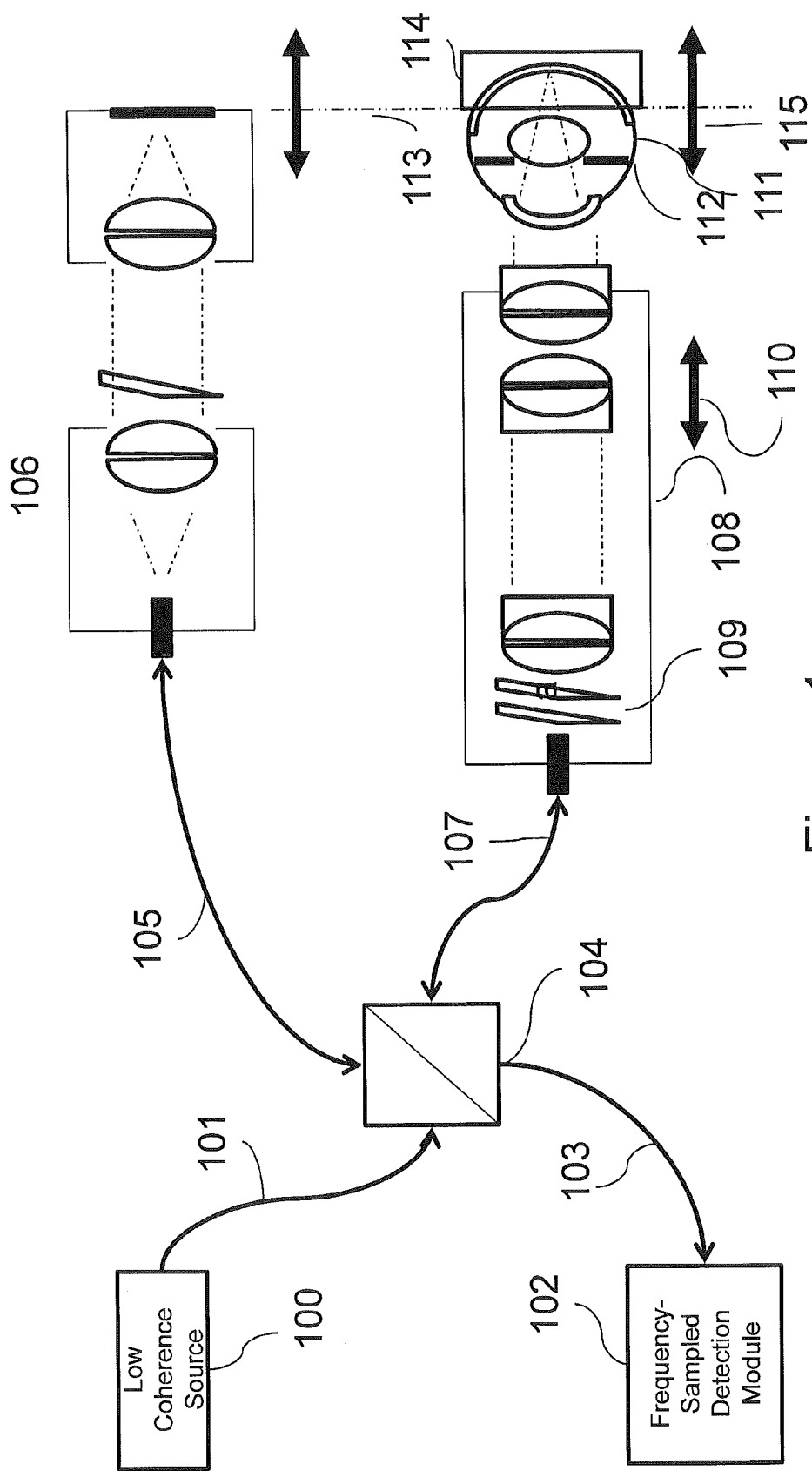
FIG. 1 is a diagram illustrating a conventional ophthalmic Fourier domain optical coherence tomography (OCT) system.

The present inventive concept will be described more fully hereinafter with reference to the accompanying figures, in which embodiments of the inventive concept are shown. This inventive concept may, however, be embodied in many alternate forms and should not be construed as limited to the embodiments set forth herein.

Accordingly, while the inventive concept is susceptible to various modifications and alternative forms, specific embodiments thereof are shown by way of example in the drawings and will herein be described in detail. It should be understood, however, that there is no intent to limit the inventive concept to the particular forms disclosed, but on the contrary, the inventive concept is to cover all modifications, equivalents, and alternatives falling within the spirit and scope of the inventive concept as defined by the claims. Like numbers refer to like elements throughout the description of the figures.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises", "comprising," "includes" and/or "including" when used in this specification, specify the presence of stated features, integers, steps, operations, elements, and/or components, but do not preclude the presence or addition of one or more other features, integers, steps, operations, elements, components, and/or groups thereof. Moreover, when an element is referred to as being "responsive" or "connected" to another element, it can be directly responsive or connected to the other element, or intervening elements may be present. In contrast, when an element is referred to as being "directly responsive" or "directly connected" to another element, there are no intervening elements present. As used herein the term "and/or" includes any and all combinations of one or more of the associated listed items and may be abbreviated as "/".

Unless otherwise defined, all terms (including technical and scientific terms) used herein have the same meaning as commonly understood by one of ordinary skill in the art to which this inventive concept belongs. It will be further understood that terms used herein should be interpreted as having a meaning that is consistent with their meaning in the context of this specification and the relevant art and will not be interpreted in an idealized or overly formal sense unless expressly so defined herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure. Although some of the diagrams include arrows on communication paths to show a primary direction of communication, it is to be understood that communication may occur in the opposite direction to the depicted arrows.

Referring now to FIG. 1, a block diagram illustrating a conventional Fourier domain optical coherence tomography (FDOCT) ophthalmic imaging system will be discussed. As illustrated in FIG. 1, the system includes a broadband optical source 100 directed along a source path 101 to a beamsplitter 104 where the source radiation is divided into a reference path 105 and a sample path 107. The reference light is returned through a reference reflection device 106 back through the beamsplitter 104 where it mixes with the light returned from a sample, such as the retina of an eye 111. The resultant wavelength dependent interferogram is directed through a detection path 103 to a detection module 102. The total spectral interferogram is processed using Fourier transforms to derive a spatial domain depth resolved image.

In contrast to a time domain OCT system, where the reference mirror scans a range over time that matches the depth range of interest for image the subject to acquire a temporal interferogram, the FDOCT system acquires a spectral interferogram from a fixed reference position 113 that is path length matched to a target axial position with respect to the subject. The spectral interferogram contains information for all depths within a window 114. The window is defined by parameters of detection as is known in the art. A scanning subsystem 108 includes a pair of scanning galvo mirrors 109 and an objective lens set with focal capabilities 110. For posterior, or retinal, ophthalmic imaging, the scanned OCT beam is directed through the pupil of the eye 112 to image the retina. An FDOCT system may include a serial acquisition of spectral information using a broadband swept frequency optical source, or a parallel acquisition of spectral information using a broadband low coherence source and a spectrometer, or a combination of these methods. A spectrometer based system is referred to as spectral domain optical coherence tomography (SDOCT) and a swept source system is referred to swept source OCT (SSOCT).

One of the difficulties in using an OCT system, and particularly a handheld OCT system, to image, for example, the retina of the eye, is that it is difficult to align, i.e. aim, the OCT beam through the pupil. Thus, according to some embodiments of the present inventive concept a system is provided including an optical coherence tomography system, an illumination system for digital photographic imaging, a digital camera for video photographic image capture, and an optional fixation target to direct the gaze of the patient.

A challenge to the design of a compact OCT scanning unit with an integrated video photographic system is to provide passively aligned optical paths, reducing the need for bulky electromechanical components, such that illumination, video focus, OCT focus and fixation focus are appropriately coordinated for all possible subjects without the need for differential focusing of the various optical subsystems.

Figure 2:
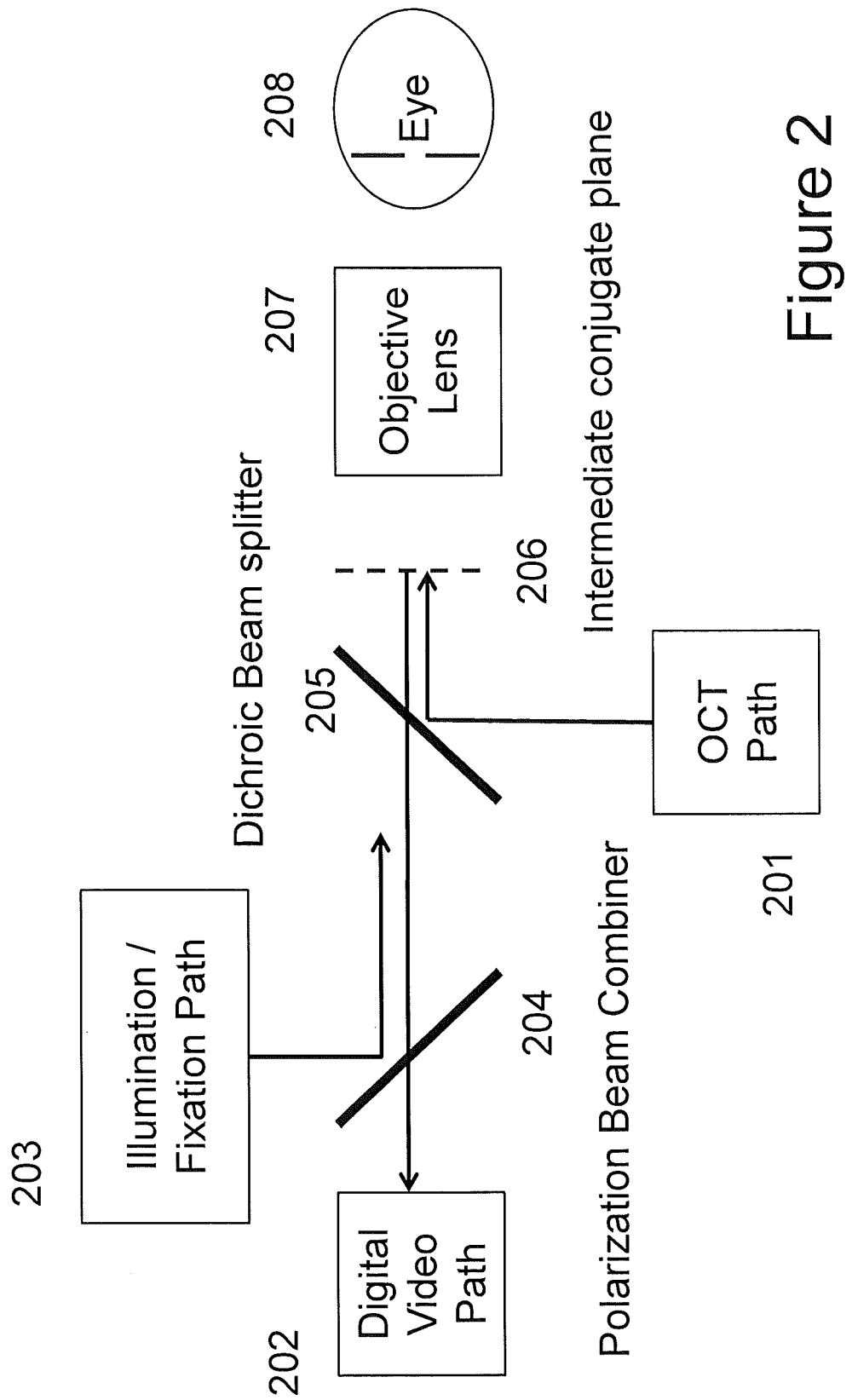
FIG. 2 is a block diagram of an imaging probe in accordance with some embodiments of the present inventive concept.

Referring now to FIG. 2, a block diagram of a system in accordance with some embodiments of the present inventive concept will be discussed. As illustrated in FIG. 2, some embodiments of the present inventive concept include a compact optical design comprising a scanning beam OCT path 201, an illumination path 203 for support of digital video capture, and a video image capture path 202. As further illustrated, the system further includes a polarization beam combiner 204 to couple the illumination and video capture paths, inhibiting specular reflections from the illuminator from interfering with the image of interest on the digital video capture device. In some embodiments, the digital image capture path and the OCT are coupled through a dichroic beamsplitter 205, share an intermediate conjugate image plane 206 path and a common objective lens 207 to image the subject of interest 208, for example an eye.

Figure 3:
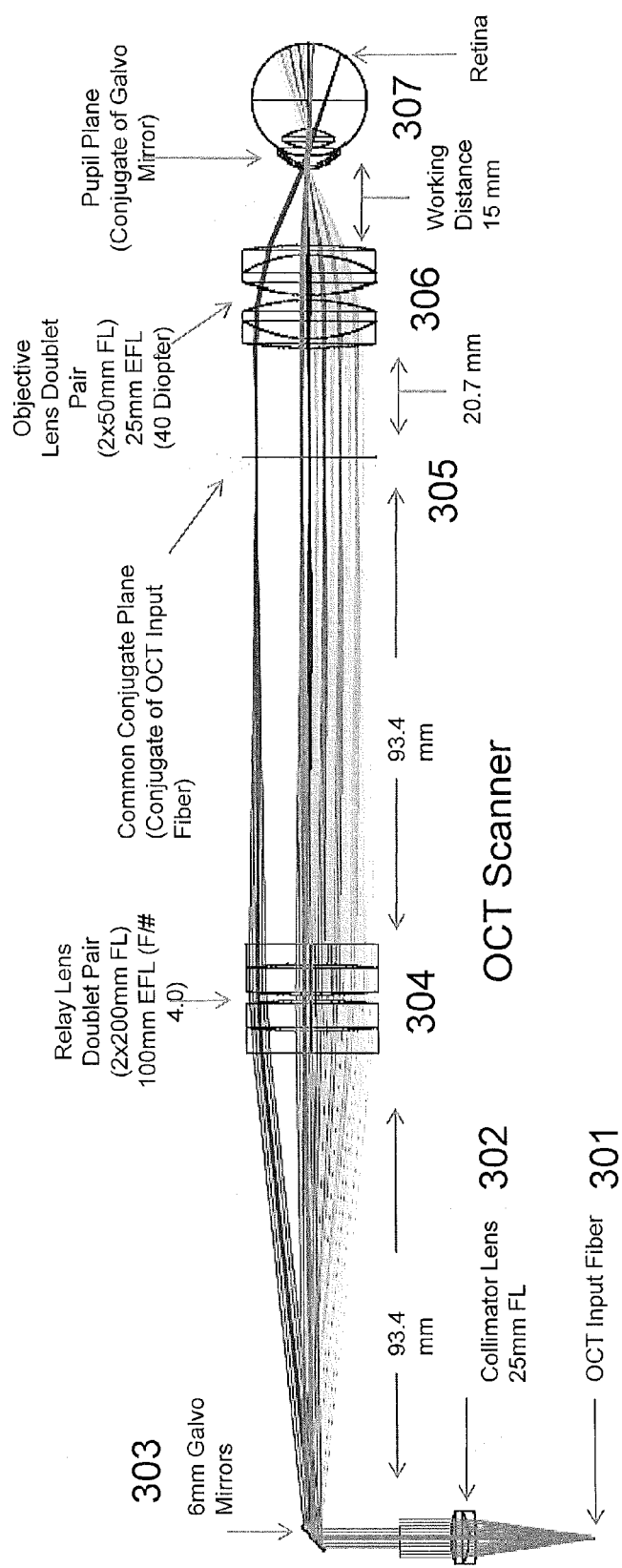
FIG. 3 is a diagram illustrating an OCT imaging path in accordance with some embodiments of the present inventive concept.

Referring now to FIG. 3, an OCT imaging path in accordance with some embodiments of the present inventive concept will now be discussed. As illustrated therein, the OCT path includes a single-mode optical fiber 301 terminated into a collimator 302, the collimated light directed to a pair of orthogonally scanning galvo mirrors 303, the scanned beam directed through a relay lens set 304 such that an image of the optical fiber input is imaged telecentrically onto the intermediate common conjugate plane (intermediate conjugate) 305. The image at the intermediate conjugate is then imaged onto the subject 307 with an appropriate objective lens 306. In some embodiments, the optical fiber 301 is a Corning HI780 single-mode fiber, the collimator 302 has a 25.0 mm focal length and the galvo mirrors 303 have a 5.0 mm or greater clear aperture. The relay lens set 304 includes a lens doublet pair with 2-200 mm FL doublets for an effective FL of 100 mm operating at f/4.0. In some embodiments, the path length from collimator 302 to relay 304 is about 93,4 mm, from the relay 304 to the intermediate conjugate 305 is about 93.4 mm and from the conjugate 305 to the objective lens 306 is about 20.7 mm (at emmetropia). The objective lens set 306 may be a 2×50 mm FL 40 Diopter doublet pair with 25 mm effective FL, operating at 15 mm working distance. The galvos 303 are conjugate to the pupil plane of the eye, and the output of the fiber 301 is conjugate to the retina.

One advantage provided by systems in accordance with embodiments of the present inventive concept discussed with respect to FIG. 3, is the ability to incorporate a final imaging objective suited to imaging a variety of targets without modification of or relative motion between the optical elements that precede the final imaging objective. The system thus defined with appropriate selection of objective lens is suited to ophthalmic imaging of the posterior (retina) or anterior (cornea) of a human eye, ophthalmic imaging of small animal (e.g. rodent) eyes, or non-ophthalmic imaging. Because of the unique challenges to imaging of a retina, discussions of embodiments herein will largely focus on retinal imaging, but it will be understood that embodiments of the present inventive concept are not limited to retinal imaging.

For retinal imaging, the wavelength of interest may be in the 800 nm to 900 nm wavelength range, or may be in the 1000 nm to 1100 nm wavelength range. A condition for artifact free OCT imaging is that the optical fiber operates in a single spatial mode at the wavelength of interest, which in turn typically requires that the second-order mode cutoff wavelength of the optical fiber be shorter than the imaging wavelength. A fiber such as Corning HI780 is suitable for imaging in the 800 nm-900 nm band.

For OCT retinal imaging, the optical system comprises a relay system wherein the galvo mirror scanning pair are located a back focal length from an optical relay lens set, the galvos 303 scan telecentrically at the intermediate conjugate 305, and the conjugate of the galvos 303 is imaged a front focal length from the objective lens set 306 at the pupil. The lateral resolution at the retina is determined by the beam stop of the optical system, at the pupil of the eye. For mydriatic (dilated) imaging, this is not much of a constraint. For non-mydriatic (not dilated) imaging, the stop is approximately 3 mm, but additional allowance must be made for off-axis aiming to explore peripheral features of the retina. The entrance pupil of the system is defined by the collimated beam at the galvos 303. In one embodiment of this system, there is a 4× demagnification of the beam between the entrance pupil (galvo) and stop (eye pupil) of the optical system. Thus, in some embodiments, the maximum galvo dimension for a 3.0 mm ocular pupil is about 12.0 mm. An optical dimension to facilitate alignment through a non-mydriatic eye with allowance for steering of the beam is to constrain the stop to one-half the ocular pupil, or about 1.5 mm This sets the galvo dimension at about 6.0 mm. Thus, in some embodiments, the stop of the OCT system may be constrained to between one-quarter and three-quarter of the natural non-mydriatic pupil diameter, and therefore the entrance pupil, or galvo diameter, to greater than about 3.0 mm and less than 12.0 mm.

The image of the optical fiber at the intermediate conjugate is a back focal length from the objective lens 306 when set to image the retina of an emmetropic subject. The scanning OCT beam is collimated exiting the objective lens set 306 and is focused on the retina by the optics of the eye. Focal adjustment for imaging hyperopic or myopic subjects, or for intentionally modifying focus to emphasize structures that may not lie within the photo-active layers of the retina, is accomplished by moving the objective lens 306 with respect to the intermediate conjugate 305.

Figure 4:
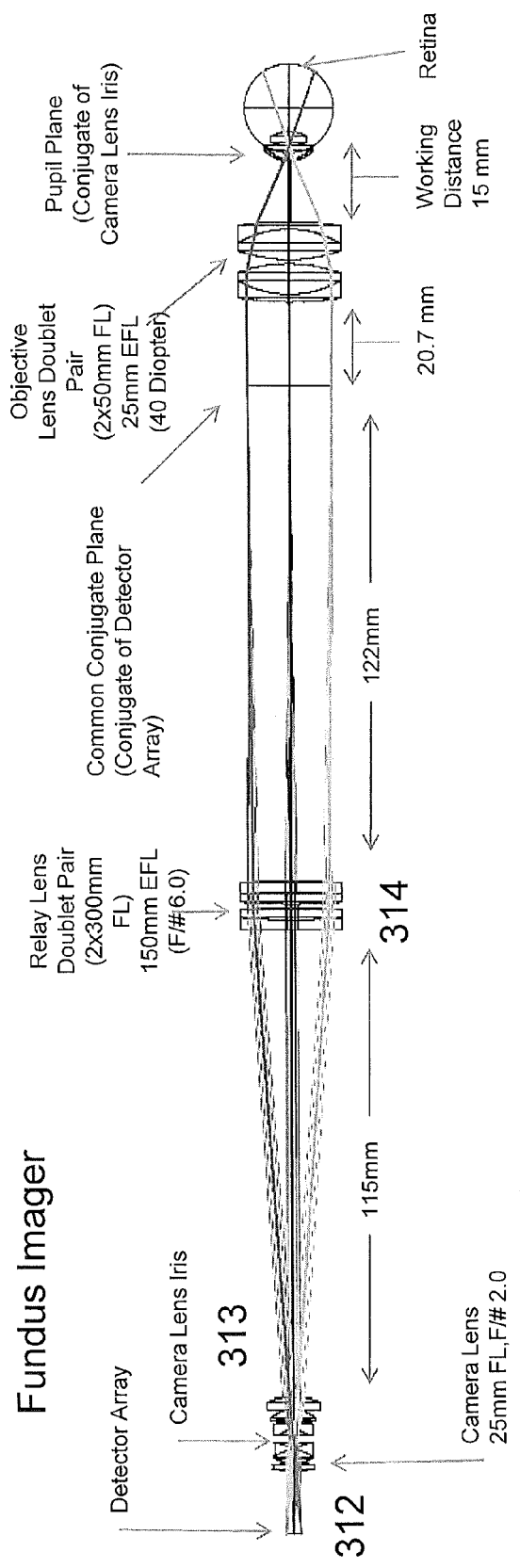
FIG. 4 is a diagram illustrating a digital video image capture path in accordance with some embodiments of the present inventive concept.

Referring now to FIG. 4, a diagram illustrating a digital video image capture path in accordance with some embodiments of the present inventive concept will be discussed. As illustrated in FIG. 4, the video capture path is designed to share the intermediate conjugate as discussed in commonly assigned United States Patent Publication No. 2009-0141237, which has been incorporated by reference above. Considered from the retina back to the image plane of the digital capture device, the retina is imaged to the intermediate conjugate through the objective lens. The image at the intermediate conjugate then images back through a relay 314 to a lens system 311 with an aperture 313, and onto the image plane of a digital camera 312. In symmetry with the OCT path, the aperture is conjugate to the pupil of the eye, and is set in relation to the illumination as will be discussed below. The camera detector plane is conjugate to the retina. Sharing as it does the intermediate conjugate with the OCT path, the video capture is both coaxial to, and confocal with the OCT path for all subjects, objectives and objective focal conditions. In some embodiments, the relay 314 includes a 2-300 mm FL doublet pair with a 150 mm effective FL operating at f/6.0. The relay may be 122 mm from the intermediate conjugate, and 115 mm from the surface of the camera lens.

The OCT path and the video capture path are coupled through a dichroic beam splitter 205 as shown in FIG. 2 discussed above. The dichroic filter acts as a high reflectivity mirror for the OCT signal and a high transmissivity window for all wavelengths of the video system. As designed, the dichroic filter is a thin film stack that operates with low polarization dependence at 45 degrees, and is transmissive for all wavelengths from about 400 nm to about 740 nm, and is reflective from about 750 nm to about 950 nm, and is designed according to the known art of thin film optical filters. The dichroic filter is positioned between the relay lens of the OCT path and the intermediate conjugate.

A challenge to the design of a compact OCT scanning unit with an integrated video photographic system is to provide a wide field illumination system for video capture that does not suffer from interfering specular reflections and whose optics neither increase system bulk nor adversely impact the OCT imaging.

Illumination systems for fundus photography are well known, and described for example in U.S. Pat. No. 5,455,644; *Fundus camera systems: a comparative analysis* by DeHoog et al. (Applied Optics 48, No. 2, 2009. pp 221-228); and *Optimal parameters for retinal illumination and imaging in fundus cameras* by DeHoog et al. (Applied Optics 47, No. 36, 2009. Pp 6769-6777). As described by Dehoog et al., there are two basic approaches to illumination in fundus photography: external and internal. These solutions are described for fundus photography alone, not in combination with OCT. These techniques, when combined with OCT, typically require an annular mirror with clear aperture equal to the diameter of the scanned OCT beam, for example, at the intermediate conjugate; necessarily such apertures in the OCT path increase the form factor of the optical system, since the outer diameter of the imaging clear aperture defines the inner diameter of the annular mirror. In other words, to maintain a compact form factor the OCT scanning width must be constrained, and this scan width directly translates to field of view.

U.S. Pat. No. 5,822,036 to Massie discusses a more compact implementation of an external illumination system using ring illumination directed through a contact lens in intimate contact with the subject cornea; the ring illumination is mediated through optical fibers positioned along the distal perimeter the objective lens. This structure is not amenable to coupling to the non-contact OCT imager of the present inventive concept.

U.S. Pat. No. 5,506,634 to Wei discusses a combined OCT system with fundus imager. However, this system utilizes external, off-axis illumination which does not lend itself well to wide field illumination or compact form factor. U.S. Pat. No. 7,140,730 to Wei discusses an on-axis external illumination method, whereby an illumination source behind an aperture projects to a beamsplitter that couples the illumination path to the image capture path. This system has disadvantages in number of optical elements, lack of control of field of illumination on the retina, and interference of the illumination path with the image capture path. Therefore, it is not generally possible to at once create a compact and wide-field combined OCT plus fundus photography using the guidance of the fundus camera prior art.

Commonly assigned United States Patent Publication No. 2009-0141237 to Izatt, incorporated by reference above, illustrates the use of an annular illuminator polarization multiplexed into a common path with the image capture device. Thus, some embodiments of the present invention provide a compact wide field illuminator that interferes with neither the OCT path nor the image capture path, yet provides uniform wide field illumination without feeding back specular reflections from the cornea to the image capture device. Furthermore, the illumination architecture provides other advantages in terms of spectrum and intensity control, as well as manufacturability as will be discussed further below.

Figure 5:
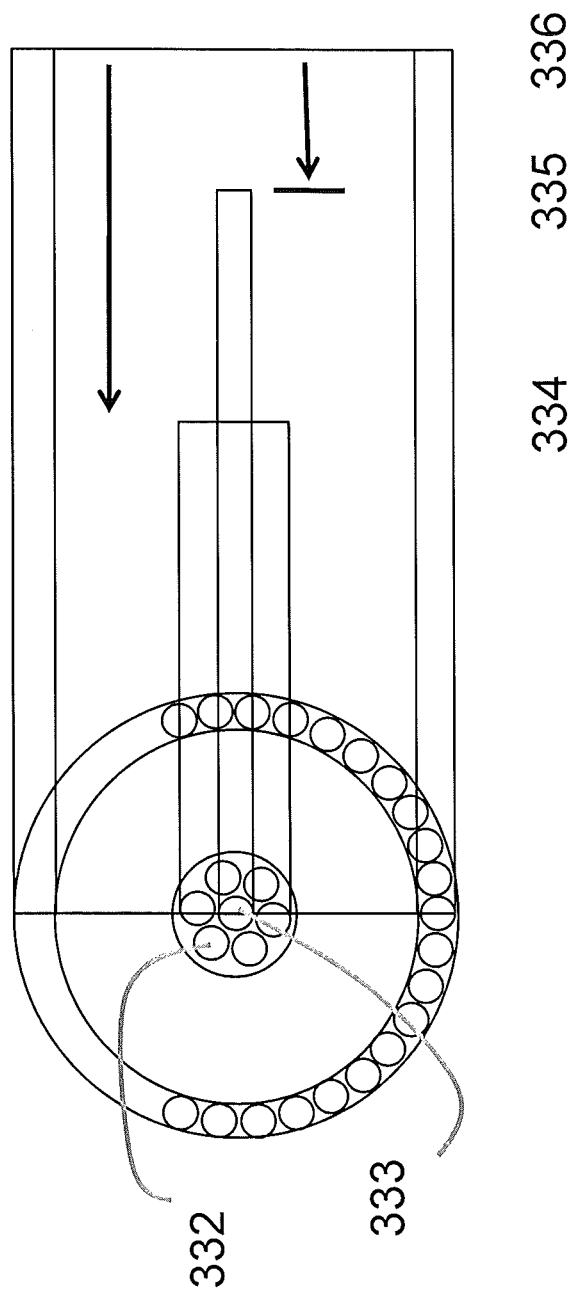
FIG. 5 is a diagram illustrating a ring illuminator including fixation and a range finder in accordance with some embodiments of the present inventive concept.
Figure 6A:
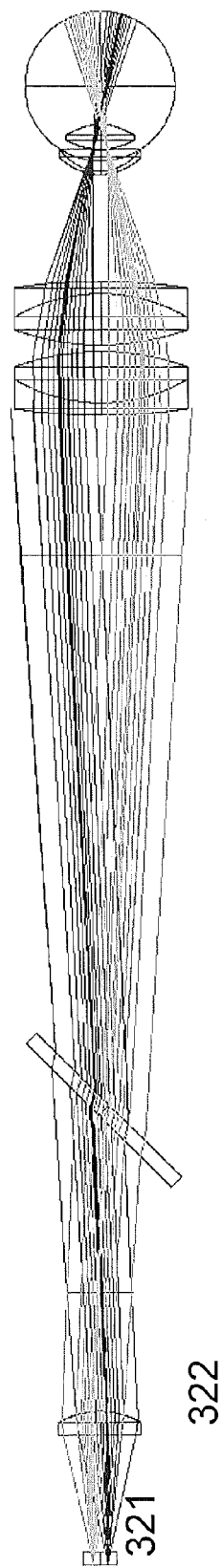
FIGS. 6A through 6C are diagrams illustrating an illuminator path in accordance with some embodiments of the present inventive concept.
Figure 6C:
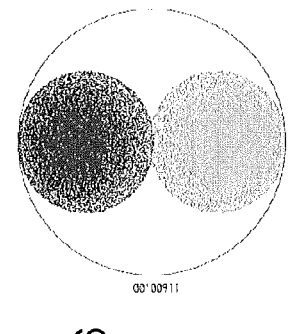
Figure 6B:
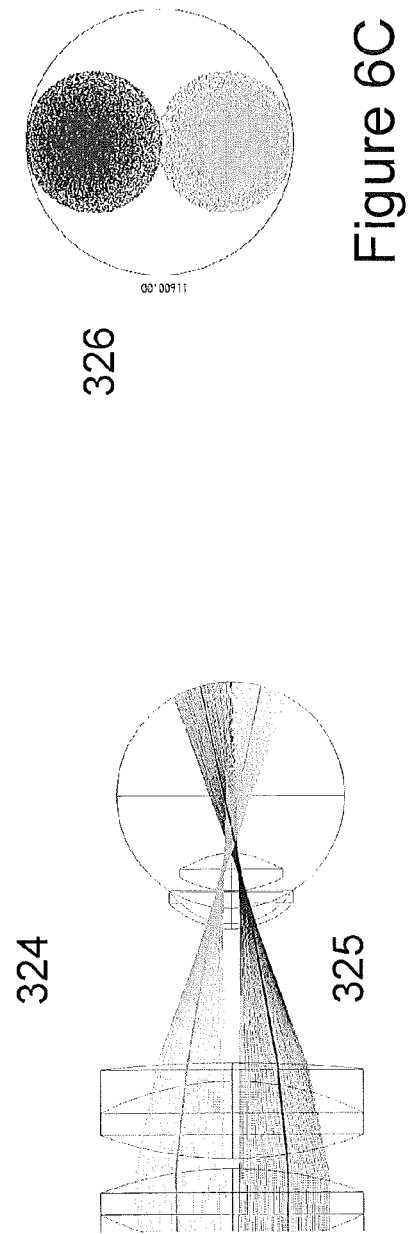

FIG. 5 is a diagram of a ring illuminator in accordance with some embodiments of the present inventive concept will be discussed. FIGS. 6A through 6C are diagrams illustrating an illumination path in accordance with some embodiments of the present inventive concept. As illustrated in FIG. 5, the fiber ring defines an annulus with an inner diameter, an outer diameter, and a radiant numerical aperture. As illustrated in FIG. 6A, the ring illuminator 321 is followed by a collimating lens 322, and the image of the ring illuminator is focused onto the pupil of the subject eye such that the outer diameter of the annulus imaged onto the pupil is less than the pupil diameter, and there remains an inner diameter of the annulus in the pupil plane. As etendue of an optical system is conserved (with appropriate consideration of refraction), there remains a deterministic relationship between the annulus dimensional magnification (demagnification) and the numerical aperture demagnification (magnification) at pupil plane. The numerical aperture at the pupil plane defines the field of illumination. By selecting appropriate ring diameters, fiber types (numerical aperture) and magnification, one can control the field of illumination as well as operating conditions, such as mydriatic (dilated) or non-mydriatic (not dilated) imaging. In some embodiments, the magnification is 1:1.09, the annular ring diameter is 2.2 mm at core center and as imaged at the cornea 324, the fibers are multimode with a core diameter of 100 µm, cladding diameter of 125 µm and a numerical aperture of about 0.22. The resultant system is suitable for non-mydriatic imaging (outer annulus diameter 325 of 2.5 mm at the pupil less than 3.0 mm optical stop) and wide field imaging (greater than about 60 degrees) illumination coverage at the retina. Illumination pattern 326 for two circumferentially opposed fibers on the retina in a human eye model of system performance is shown in FIG. 6B and en face in FIG. 6C. Additionally, the versatility of this illumination and imaging system is shown by the illumination pattern on a mouse retina, where the only difference in the systems is in the objective lens. The objective lens design is optimized for the spherical, or ball-lens, phenotype of the rodent, as described in commonly assigned United States Patent Publication No. 2009-0268161, incorporated by reference above. Further still, the illumination system provides uniform illumination when used in conjunction with a telecentric objective lens, for illumination of a cornea or other tissue structure that is preferably imaged with a telecentric imaging system.

The digital video capture subsystem in accordance with some embodiments discussed herein serves multiple purposes. The first purpose is to provide a real-time video image to aid the alignment of the OCT beam. For this application, low level optical irradiance is desired to keep the total irradiance at the retina below the Maximum Permissible Exposure (MPE) for eye safe operation over extended imaging periods. The maximum permissible exposure (MPE), as defined in the American national standard for safe use of lasers (ANSI Z136.1), is a function of wavelength and optical power. It is desirable to illuminate in the infrared or near-infrared with a minimum optical power. Particularly when the OCT system is scanning simultaneously with the video illumination, the video illumination will be at the lowest level suitable to derive an image suitable for alignment.

The second purpose of the digital video capture subsystem is to use the digital video image for exploratory ophthalmoscopy. In this mode, the OCT signal may be turned off, and the radiant power of the video illumination turned up to facilitate higher contrast imaging. In this mode, the system functions as a non-contract fundus camera.

A third purpose is to capture a photographic reference image against which to compare the OCT depth-resolved image. The low-level alignment signal and the intermediate level exploratory signal may be sufficient to capture a nominal reference image. It may also be desirable to provide a significant increase in optical irradiance for a short interval in order to capture a brighter or higher contrast image. Furthermore, it may be desirable to provide visible illumination during the period of image capture in order to provide a color photograph as clinical record.

The fiber ring illuminator enables flexible placement and selection of the light source or light sources remote from the scan head, further supporting compact design of the scan head. Additionally, the remote coupling of the light source simplifies electronic design and reduces complexity of electrical systems and power delivery within the scan head. The development of light emitting diode (LED) technology has simplified the selection and management of illumination sources. In some embodiments, a single LED is used at a wavelength between about 650 nm and about 740 nm coupled into a fiber bundle at the proximal end of the fiber ring illuminator cable. In these embodiments, the bundle consists of fifty-five multimode optical fibers bundled together at the proximal end of a cable, and distributed into a ring at the distal end. A 30 mW LED is sufficient including coupling losses to provide the desired illuminance on the retina, though lower powers may also be acceptable. The integrated optical output power from the objective lens may be constrained to 50 µW, so that when combined with 700 µW of OCT power the MPE for long term exposure (30,000 seconds) is not exceeded. The 50 µW power level is sufficient to provide a visible image of the retina at video rates.

The near-infrared illumination at low power level is satisfactory for exploration and alignment using the digital video signal. However, higher intensity is desirable for higher contrast and higher signal to noise images. In some embodiments of the present inventive concept, the illumination intensity level may be raised, and the exposure on the digital capture device adjusted according to well known means in order to capture and display a higher quality image.

In order to keep the system operating within the MPE for the desired examination period, the system operation allows an OCT-only examination, a video image capture period only, a combined operation mode, and a short duration flash operation mode of the digital imaging system. Combined operation is discussed above. In video capture only mode, the OCT signal may be turned down or off, and the ring illumination source turned up to 500 µW, the precise level determined in conjunction with the sensitivity of the image capture device, the turbidity of the optical medium, and the desired exposure period. In flash digital image capture mode, a brief cycle of elevated power, for example 5 mW, or 2-3 W/cm$^2$, to acquire a snapshot may be applied.

Figure 7:
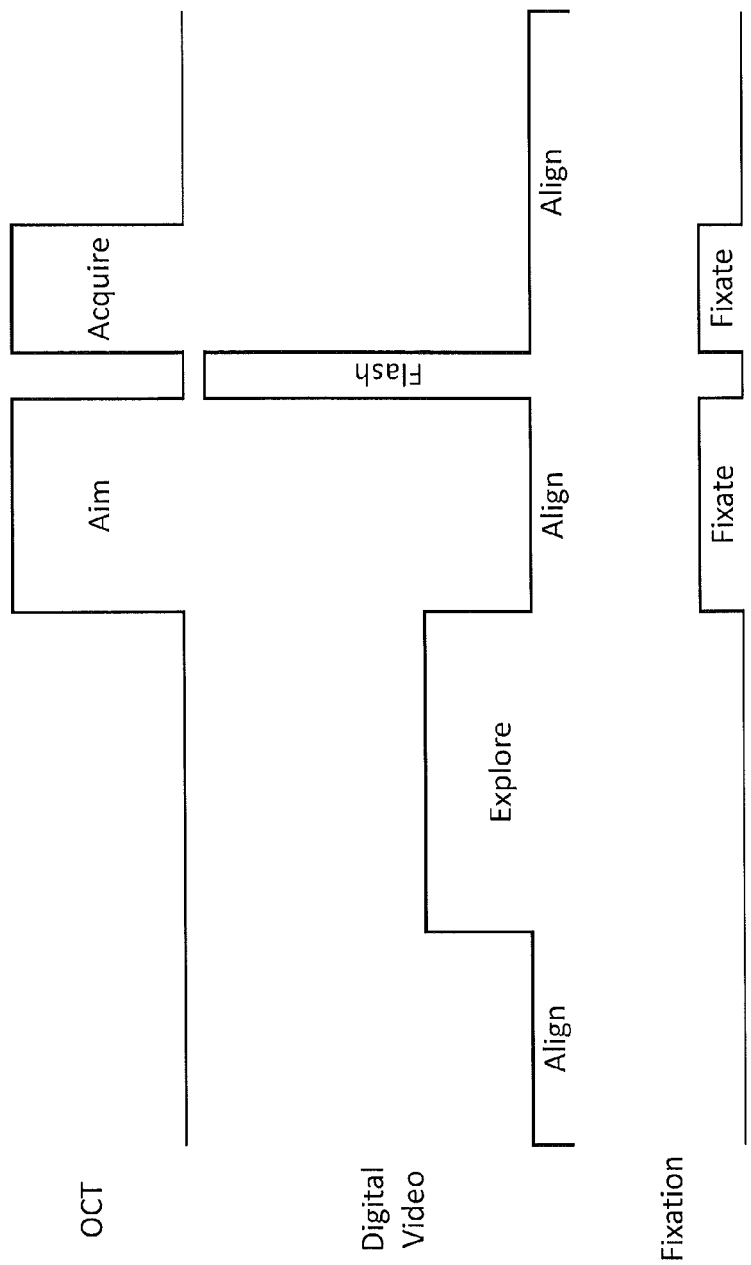
FIG. 7 is a timing diagram illustrating timing and intensity in accordance with some embodiments of the present inventive concept.

A particular imaging cycle may consist of the following: exploratory examination of the fundus in video image capture mode, with OCT off to identify a region of interest; combined operation mode, with the OCT operating in a two-orthogonal-axis aiming mode and the video image capture operating in low power mode as an alignment support device, in order to locate the OCT beam on the region of interest; a flash short duration high intensity image acquisition with the digital image capture device, OCT signal off, followed by an OCT image acquisition sequence with low level video illumination and digital image capture on or off, as desired. This is illustrated in the timing and intensity diagram of FIG. 7. It will be understood that other imaging sequences are possible and may be established as pre-programmed sequences or may be photographer controlled.

A third purpose of the video capture subsystem is to enable full color or hyperspectral photography for emphasizing various features of the imaged structure and various depths of the imaged structures, such hyperspectral images providing additional clinical diagnostic value when correlated to the depth resolved structural OCT images.

A fourth purpose of the video capture subsystem is to enable fluorescent image photography for emphasizing various features of the imaged structure and various depths of the imaged structures, such fluorescent images providing additional clinical diagnostic value when correlated to the depth resolved structural OCT images.

It is well understood in the art that full color imaging is desirable to provide diagnostic images consistent with clinical expectations, for example as derived from indirect ophthalmoscopy and historical expectations from a generation of film-based fundus photography. It is therefore desirable to present an imaging mode consistent with the art, and further to provide correlated imaging between such video fundus photographs and the depth-resolved information provided by OCT.

In some embodiments of the inventive concept imaging optics are optimized for high-quality OCT images, that is an independent OCT path that couples to the video imaging path through a polarization independent dichroic beamsplitter, which may be a thin film filter. The imaging objective is optimized for high resolution color-corrected imaging of the OCT signal. Additionally, the dichroic beamsplitter is transmissive without significant color centers for all visible wavelengths shorter than the reflection edge, as discussed above. The imaging objective must also be transmissive for the illumination and digital image capture wavelengths, thus the imaging objectives are broadband antireflective coated, for example, from about 400 nm to about 950 nm. As discussed, the lateral resolution of the digital image capture subsystem may be suboptimal when the system is optimized for the OCT imaging. While high performance broadband imaging optics may be designed, there will in general be some trade-off to be made in choice of best performance operating range and cost. It is understood that the trade-off to optimize for superior OCT imaging at some cost to the digital image capture is one of many choices.

With the broadband transmission defined, it then is desirable to offer specific flexibility to select illumination wavelengths. One option is to illuminate directly with halogen or Xenon lamps coupled into the proximal end of the illuminator bundle. Another convenient choice is to use the new generation of white light LEDs. Another convenient choice is to use a multiplicity of monochromatic sources, such as would be available by filtering the output of a halogen or Xenon lamp, or by selecting from available monochromatic LEDs. On such choice of LEDs would be to illuminate with a combination of a blue, a green and a red LED. This combination may be used in unison, or cycled in a sequence, and may be captured in a black & white camera or a color camera.

Fundus Image Colorimetry in accordance with some embodiments will be discussed. Inherent in both the Fundus Illumination System and the Fundus Illumination Light Guide is the ability to accommodate a wavelength range of about 400-1000 nm with no change to the design parameters. Thus multispectral imaging of the fundus or other target tissue is possible. Given that light penetration into tissue in general, and the retinal tissue specifically, is wavelength dependant, a series of images can be built up using selective wavelength to create a visual depth volume. In addition, selective wavelength imaging at a specific depth within the retina may be used to create a visual filtering of the fundus image to locate pathologies to better guide the OCT scanning. Adding a monochrometer input to the illumination system or other wavelength selection mechanism such as turning on or adjusting the power level of individual monochrome LEDS provides the capability to "dial" thru the wavelength range while viewing the live fundus image to see if pathologies of interest appear could be of great value. This function dubbed "ChromaFundus" would allow the operator to selectively match the OCT image with a corresponding Fundus image taken at a selected wavelength. Likewise, if the source were scanned through the wavelength range the display aspect of such data could result in the multispectral images stacked just as the OCT data and depth windowing could be used to display pathologies of interest.

In general, a black&white camera will offer greater imaging resolution. A cycled acquisition of monochromatic images may be captured, and a pseudo-colored image recreated in post-processing by creating a weighted average image from the multiplicity of monochrome images. An appropriate camera is the Imaging Source DMK 72BUCO2 monochrome CMOS camera. This Fundus Image Colorimetry has many advantages in the ability to obtain the highest quality image per exposure, and to tune the color quality to meet clinical objectives. One such objective is to obtain images with a color temperature similar to accepted commercial clinical systems.

The combination of design elements, including passive registration of the digital video illumination optical path, the digital video image capture path, and the OCT path, supports real-time coordination of the OCT region of interest to pathologies observed on the digital image capture device.

Figure 8:
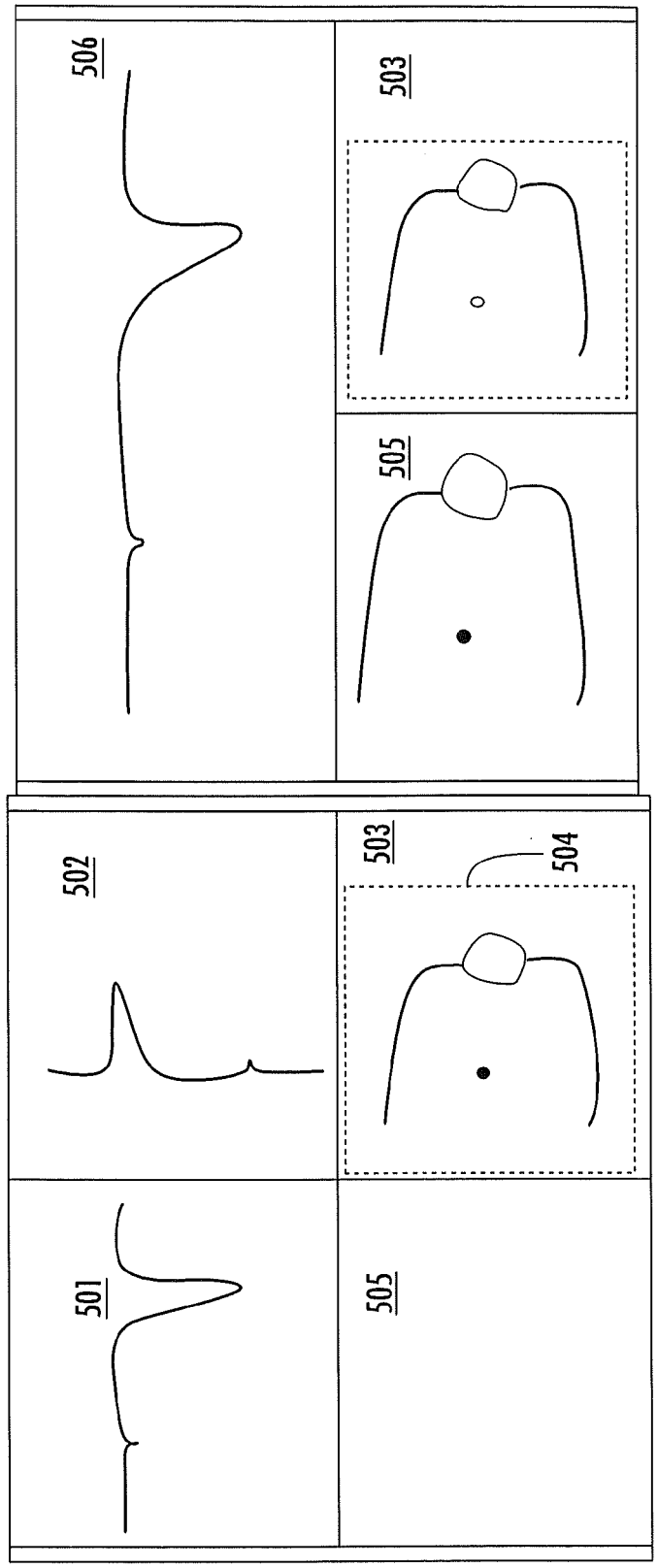
FIGS. 8A and 8B are diagrams illustrating a display window in accordance with some embodiments of the present inventive concept.

Referring now to FIG. 8, display windows in accordance with some embodiments will be discussed. As illustrated in FIG. 8, such a system and method include an image presentation window for the OCT aiming mode image, with horizontal 501 and vertical 502 orthogonal views and an image presentation window for the digital image capture image mode 503, together with another window for presentation of an en face intensity projection of OCT depth resolved data 505. As discussed, the OCT and digital image may be simultaneously live (in contrast to SLO images that have a longer duration capture period). Dynamic Scan Control is facilitated through a graphical box 504 overlaid on the video capture window that shows the sub region of the video field of view that is the current OCT field of view. The photographer may dynamically control the OCT field of view—central location and extent of field of view—by dragging the location and boundaries of the graphical box overlay. The OCT scanners are configured to respond in real-time, and the resultant OCT image aiming mode will update automatically in real-time. When the final region of interest is identified, the OCT image capture is initiated, and the image is then acquired precisely on the region of interest as observed on the digital image capture device. The image so displayed on the video image capture device may be any of the modes mentioned, including a monochromatic image acquired at any one of the available illumination wavelengths, a true-color image derived from white light illumination or selected color combination, or a composite color image acquired and derived by a combination of wavelengths.

The ability to control illumination wavelengths enables video fluorescence imaging, and in particular simultaneous OCT, Doppler OCT as discussed in U.S. Pat. No. 6,006,128, and fluorescence imaging. This synergy provides coordinated information on the structure of the tissue, the flow in the retinal vasculature, pooling of blood, presence of fluorescent labels, and presence or lack thereof of natural fluorescent chromophores that have clinical diagnostic value. In some embodiments, a filter wheel is added in front of the digital camera, for example in the proximity of the aperture, a position of minimum filter surface area, and therefore size and cost. The filter wheel comes at no cost to the OCT performance.

A 480 nm fluorescence source is incorporated into the selection of illumination sources to support both fluorescien imaging, for fluorescien angiography (FA), for example, and also in support of auto-fluorescence (AF) imaging. The source output set to 2 mW/cm$^2$ on the retina is sufficient for excitation as discussed in *Noninvasive Imaging and Monitoring of Retinal Pigment Epithelium Patterns using Fundus Autofluorescence—Review* by Framme, et al (Current Medical Imaging Reviews, 2005, no. 1, pp 89-103). For FA, an emission filter with a 530+43 nm bandpass at the camera aperture plane is appropriate. For AF, a long pass filter passing wavelengths longer than 500 nm is appropriate. Other sources of excitation and emission filters may be appropriate for imaging of other labels and chromophores.

In addition to coordinated focal requirements of the OCT and video capture capability of the subject device, it is desirable to provide certain image stabilization features for the system, particularly for handheld operations.

SLO has been used to stabilize OCT image location, for example, in United States Patent Publication No. 2010/0053553 to Zinser, and pupil tracking has been used to for eye tracking using video technology. A disadvantage of SLO-based eye tracking is that image acquisition is relatively slow (e.g. 1 second per en face frame). A disadvantage of pupil-based eye tracking for retina imaging is that the image recorded (e.g. the pupil) is not the same as the target image (e.g. the retina).

Therefore, an additional application of the video image is to provide low-latency feedback to the OCT scan position for image stabilization. One useful mode for providing this feedback is to identify and lock on to the optic nerve head, tracking changes to the optic nerve head within the image frame, and utilizing this changing position to direct the OCT scanners.

Figure 9:
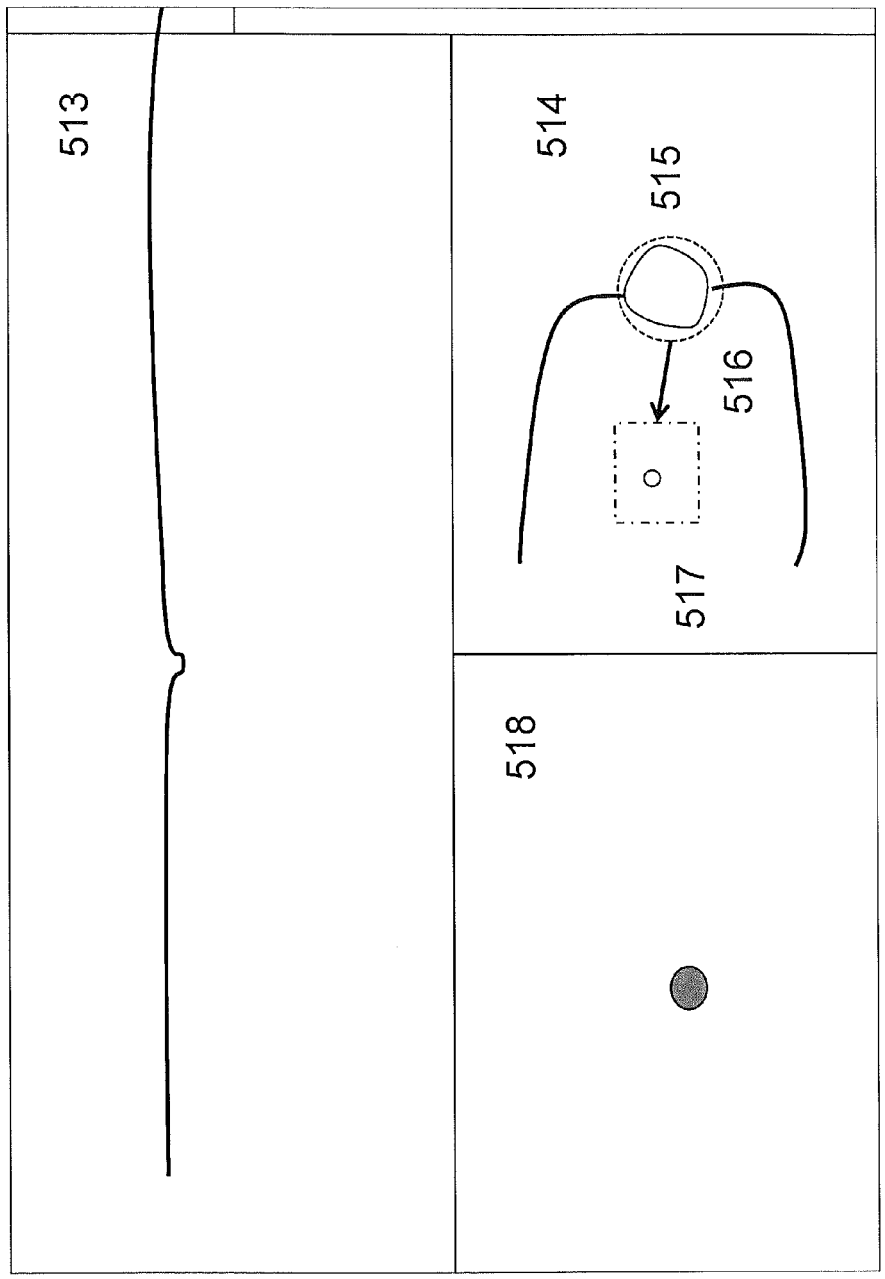
FIG. 9 is a diagram illustrating application of video eye tracking in OCT in accordance with some embodiments of the present inventive concept.

Eye Tracking will now be discussed. As the subject eye moves the image on the digital image capture window moves. The motion within this window is tracked using methods known in the art. For example, a well defined landmark, such as the optic nerve head, is software-identified in a manner similar to pupil tracking algorithms. During aiming mode, a vector is computed that identifies the relative position of the OCT region of interest to the landmark. This vector may be recomputed during aiming mode as the region of interest is modified through manipulation of the dynamic scan control graphical box. During OCT image capture mode, relative motion between the scan head and the patient will cause motion of the position of the landmark. At this point the vector is fixed, and a signal is sent to the OCT scanning mirrors to adjust the position of the acquisition window such that the relative position of the OCT field of view and the landmark observed on the digital capture device remains stable. This behavior is illustrated for example in FIG. 9. As illustrated therein, in the video window 514, the software automatically identifies the optic nerve head (ONH) and draws a circle 515 around the ONH. The user draws a box 517 around the region of interest, and the system scans the region as shown in B-scan 513 and en face view 518. The system computes a vector 516, and as the ONH identifier 515 moves, a change vector (not shown) is applied to the OCT galvos to keep the position of the region of interest stable.

An interferometer stabilization feature will now be discussed. OCT is an interferometric system, and Fourier domain OCT (FDOCT) in particular requires coordination and maintenance of a sample arm length and a reference arm length.

Additionally, the sample arm length includes the working distance between the objective lens and the subject. It is therefore desirable to provide the photographer with an indicator of current working distance with respect to the target working distance.

Figure 10:
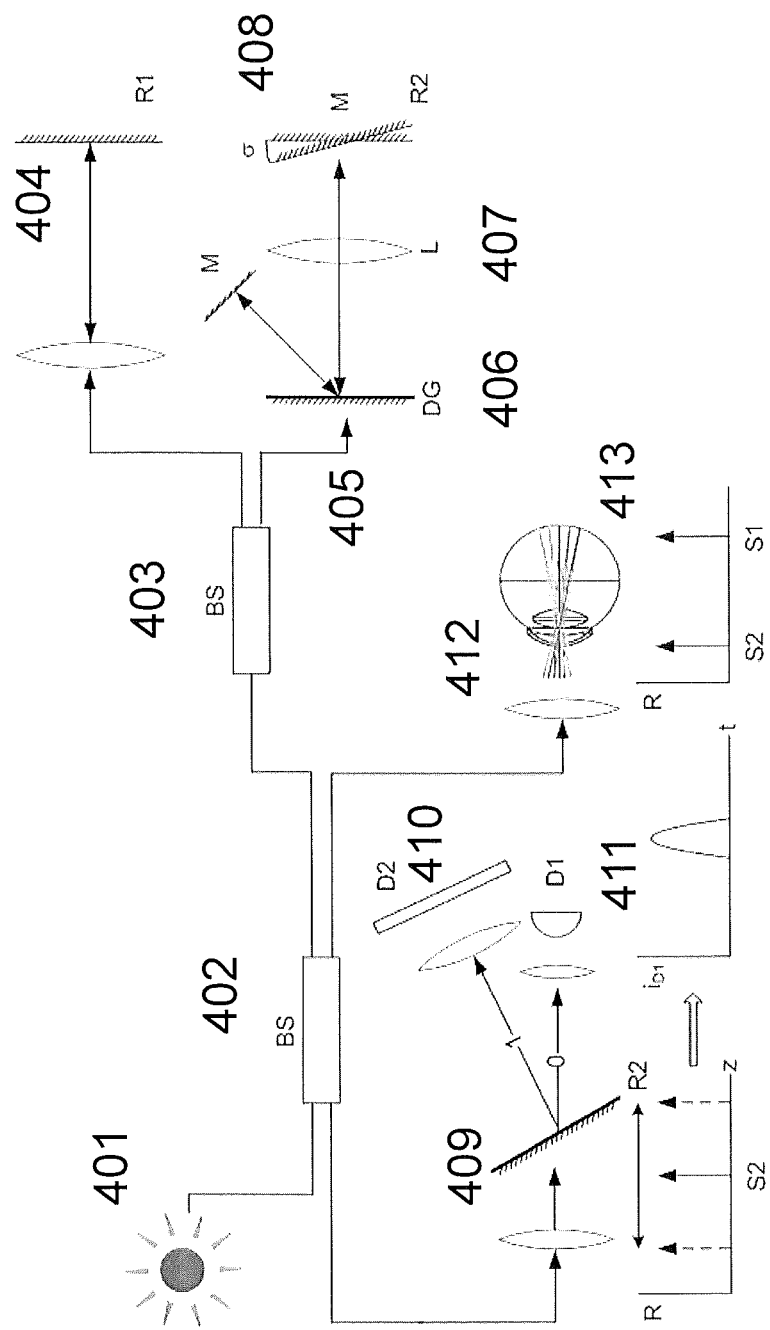
FIG. 10 is a diagram of a Spectral Domain OCT (SDOCT) system including a range finder in accordance with some embodiments of the present inventive concept.

Referring now to FIG. 10, an SDOCT system in accordance with some embodiments of the present inventive concept will be discussed. The SDOCT system includes a supplemental time-domain rapid scanning optical delay (RSOD) system. As illustrated in FIG. 10, the SDOCT system includes a Beam Splitter (BS) 402, a first reference Arm (R1) 404 for retinal imaging, a second RSOD Reference Arm (R2) 408 for corneal imaging, a Mirror (M), a Diffraction Grating (DG) 406, RSOD objective Lens (L) 407, RSOD mirror angle (s), Sample signal from retina (S1), Sample signal from cornea (S2), Point Detector (D1) 411 for capturing the fundamental through the diffraction grating, and SDOCT array detector (D2) 410.

Correct location of the imaging lens relative to the patient's cornea may reduce vignetting and ensure accurate lateral calibration of the image. In embodiments illustrated in FIG. 10, a real-time range finder is used to guide the photographer to the correct working distance. A second reference light path R2 404 matched to the design working distance enables detection of the corneal surface. The second reference path 404 is part of a time domain OCT system that shares the optical path with the primary imaging Fourier domain OCT system. A scanning reference path, for example, a Rapid Scanning Optical Delay Line (RSOD) 405 (Kwong et al, Optics Letters, 18, no. 7, 1993, pp. 558-560) in R2 is pathlength matched to the working distance, and scans through a 1.0 cm distance for corneal ranging. As R2 scans, the time averaged signal at the detector has a peak at the cornea. A visual or audio directional indicator in the software may indicate the position of the cornea relative to the probe tip; as the probe approaches the designed working distance, the corneal peak will be strongest, and the visual or audio cue to the operator will indicate that the proper working distance has been achieved.

In some embodiments, the RSOD may be designed with the following parameters: for an angle σ of 22.5°, a mirror offset 408 of 3.2 mm, an objective 407 focal length of 50 mm, a center wavelength of 840 nm, a grating 406 pitch of 600 lines/mm, and the path length swept by the RSOD is 10 mm.

A sweep rate of greater than 30 kHz is practical but not necessary; a 100-200 Hz update rate should be sufficient, indicating a lower cost scanning mirror will be sufficient for the range finder.

In some embodiments, the range-finder shares the primary OCT source 401 and optical path 402 as shown in FIG. 10, with a fraction of the light in the reference arm peeled off from the primary Fourier domain reference arm by a beamsplitter 403 to the time domain, e.g. RSOD, reference arm. Between 25% and 50% of the primary reference arm power may be diverted to the time domain path without adversely impacting the primary imaging OCT system, as generally the reference arm path is attenuated, particularly in an ophthalmic OCT system. The range finding and Fourier domain OCT paths are sufficiently separated such that no mixing between the two paths will occur, but care must be taken to match the pathlengths S2 (sample path to the cornea) and R2 such that the signal from the cornea does not interfere with the retinal image. The signal from the cornea 412 will be very weak when the objective lens is set to imaging the retina 413. This is satisfactory for range finding, as the relatively slow refresh rate allows sufficient averaging to pull out the weak signal, and since this range finding is not for image generation, and range finding accuracy can be to the millimeter level, the system can tolerate significantly more noise than would be acceptable in an imaging system.

This method uses the OCT light to determine the distance to the cornea and thus does not require an external light source or additional power on the eye. There is no change to the sample arm optics or probe, while there is a moderate change to the spectrometer. Generally, high efficiency gratings 409 are used in spectrometer design, and the undiffracted fundamental diffraction order is cast onto a light trap to avoid stray light hitting the array detector 410. For the range finder, this fundamental order is directed to a point detector 411 in the body of the spectrometer, rather than a light trap. In one embodiment, approximately 3% of the sample light is lost through specular reflection off the cornea, and this becomes the light for range finding. 5% to 20% of the signal incident on the spectrometer is captured on the range finding detector, and demodulated with techniques well known in the time domain OCT art.

In further embodiments, the range finder and the OCT imaging system are at different wavelengths, and the range finder signal couples to OCT signal through the dichroic filter; the range finder signal may be at a near-infrared wavelength nominally shorter than the OCT signal. In order to focus the range finding signal preferentially on the cornea, a single mode fiber 333 with 0.12 NA is positioned within the clear aperture of ring illuminator of FIG. 5, with the distal end position placed a distance of 3.7 mm 335 behind the illumination fiber ring; in this geometry the range finding signal focuses directly on the cornea of the eye with a spot diameter on the cornea is approximately 60 µm. Construction of the ring illuminator to incorporate the independent ranging signal as well as a fixation light 332 (discussed below) is shown in FIG. 5.

A combined time domain—spectral domain system for monitoring changes to the front position of the eye in an eye length measurement device is discussed in U.S. Pat. No. 7,400,410 to Baker. In contrast to Baker, the embodiments of the present inventive concept is directed towards providing guidance to the photographer for correct positioning of the OCT imaging probe to the target in order to maximize image quality by minimizing vignetting through the subject pupil. In contrast to Baker, some embodiments of the present inventive concept allow full range scanning of the retina, whereas Baker is designed for a point measurement in order to measure a length of the eye, not the use of the combined technologies for ranging or for ranging plus imaging.

Figure 11:
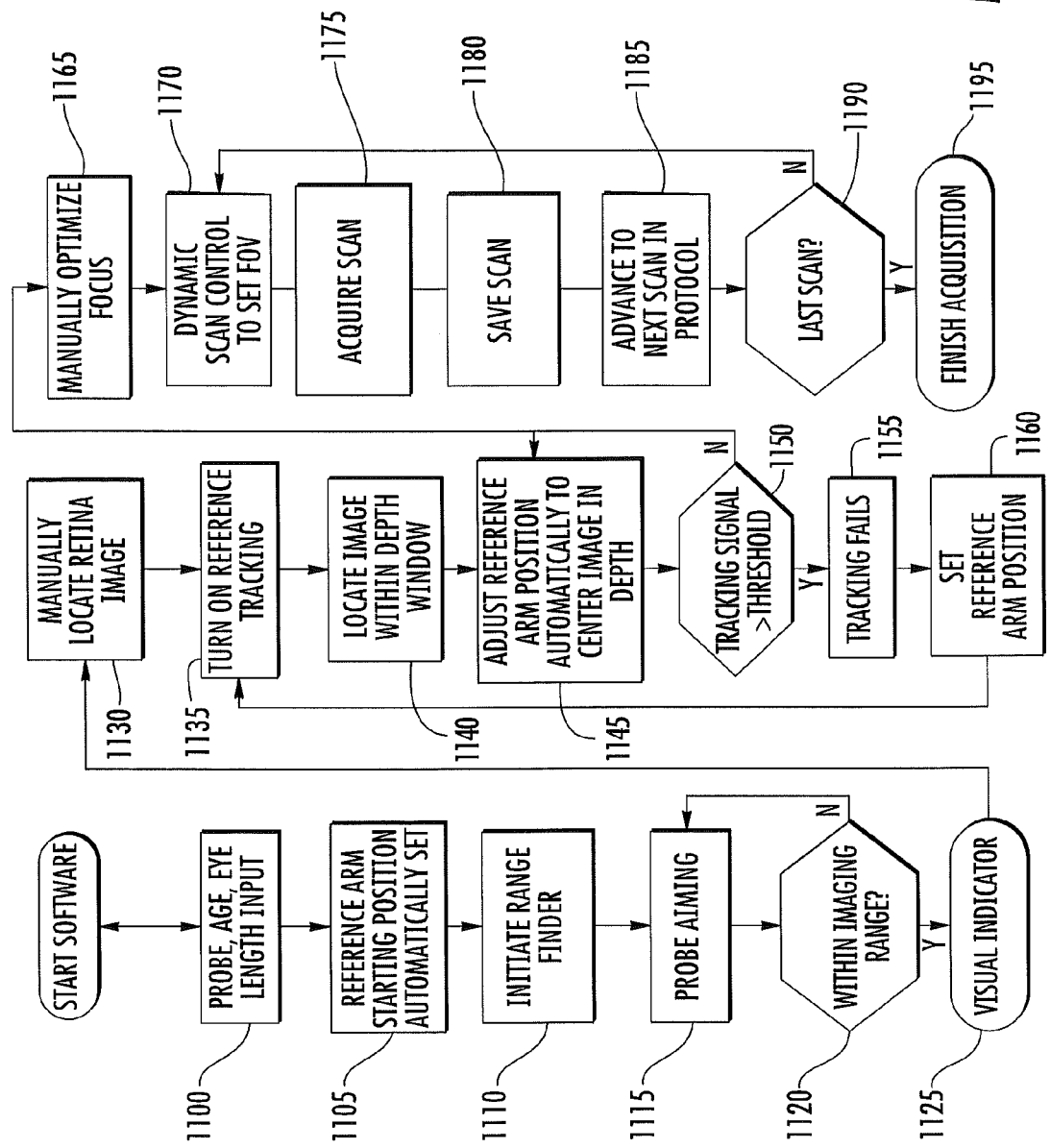
FIG. 11 is a flowchart illustrating operations of a range finding controller in accordance with some embodiments of the present inventive concept.

Referring now to FIG. 11, methods for a complete control architecture that includes range guidance in accordance with some embodiments of the present inventive concept is illustrated in a flowchart. Range finding is intended as an alignment aid for either or both of the OCT imaging subsystem and the digital video imaging subsystem, both of which benefit through minimized vignetting at a proper working distance.

Operations of systems in accordance with some embodiments of the present inventive concept will be discussed with respect to FIG. 11. As illustrated in FIG. 11, after the software is started, operations begin at block 1100 by inputting information with respect to the subject to be imaged. The information may include, for example, age of the subject, eye length of the subject and the like. Operations continue at block 1105 by automatically setting the initial reference arm position. The range finder is initiated (block 1110). The user aims the probe (block 1115) and it is determined if the probe is within the imaging range (block 1120). If it is determined that the probe is not within the imaging range (block 1120), operations return to block 1115 and repeat until it is determined that the probe is within range (block 1120). If it is determined that the probe is within range (block 1120), operations continue to block 1125 for a visual indicator. The retina image is manually located (block 1130), and location confirmed using, for example, a foot pedal. Once the reference image is located (block 1130), reference tracking is turned on (block 1135). An image is located within the depth field (block 1140). The reference arm position is automatically adjusted to the center image in the depth (block 1145).

Tracking signal is analyzed to assure that the tracking remains within range by testing the tracking signal against a threshold (block 1150). If it is determined that the threshold has not been exceeded, operations continue to block 1165 where the focus is manually optimized. The field of view (FOV) is set using, for example, dynamic scan control using, for example, a mouse, a touch screen, a foot pedal, or an on-probe control (block 1170). The scan is acquired (block 1175) and saved (block 1180). Using, for example, a pedal, the system is advanced to the next scan in the protocol. It is determined if the last scan had been acquired (block 1190). If it is determined that the last scan has been acquired, the acquisition is finished (block 1195).

If it is determined at block 1150 that the threshold has been exceeded, operations proceed to block 1155 where it is concluded that tracking has failed. The reference arm position is set (block 1160) and operations return to block 1135 and repeat until the tracking signal has not been exceeded (block 1150).

Another variable in the interferometric system that makes up OCT is finding and controlling the reference path length to match the sample path length. In time domain OCT, the reference arm always scans through the path matching conditions by design. Fourier domain systems operate differently, with fixed reference paths designed such that the path matching condition that produces an undesired DC signal is positioned conscientiously with respect to the depth range of interest. For imaging of mature eyes or anterior surface structures, variability of reference arm positions has not generally been a practical problem. Even for the variability of mature eye lengths in an adult population, this has not been a problem in tabletop imaging where range finding and vignetting is not a challenge, and where eye dilation is common. Reference arm optimization in handheld imaging, and particularly in pediatric imaging as well as in cases of severe eye distortion, for example in severe myopia, is more of a problem.

The use of range finding assures proper location of the objective lens with respect to subject eye, assuring that pivot of the scanning galvos is conjugate to the pupil for the maximum scan range on the retina. The first surface of the retina, the Inner Limiting Membrane (ILM), the layer between the inner retina and the vitreous, is visible with high contrast to the vitreous. This boundary layer is readily identified in linewise (A-scan) signal processing by searching for the first positive intensity gradient above a noise threshold at a search position starting a prescribed and slight distance away from the DC signal (for example 20 pixels or 60 micrometers); the position of this ILM may be fed back to an electromechanical controller for the reference arm, assuring optimum stable positioning of the retina in the Fourier domain imaging window. The electromechanical control of the reference arm can be guided by the position of the ILM on a single A-scan, by an operation, such as averaging, of the position of the ILM on a multiplicity of A-scans, or by a centroid position of tissue in a region above, below, or surrounding the identified ILM on a single A-line or multiplicity of A-lines, as examples.

The combination of range finding plus reference arm control increases the likelihood of optimum image acquisition even with the photographer-to-patient relationship is not perfectly stabilized. Furthermore, the eye length may be directly inferred from the range reference arm position and the image reference arm position. This is particularly useful for accurate lateral calibration of the retinal image. In general, the scanning system is calibrated by determining the degrees of deviation of the mirror per unit of applied voltage, and an estimate of eye length is used to convert the angular scan range to a lateral value on the surface of the retina. In some embodiments of the present inventive concept, real-time knowledge of the scanner position and eye length is used to accurately calibrate the lateral scan range during imaging.

It may be further desirable to provide a fixation target to direct the gaze of the subject. As discussed in U.S. Patent Publication No. 2009-0141237, a dichroic filter is used to separate the path of a visible fixation display, for example, an OLED or LCD display, in physical space and in wavelength space, from the OCT, and video illumination and capture paths. Such a configuration remains useful for providing general fixation guidance as well as video stimulation signals. Video signals in such a capacity may be useful for maintaining the attention of the subject, and could also be used as a stimulation signature in cooperation with a multifocal electroretinography (ERG) session to measure electrical activity related to retinal stimulation.

An internal fixation target is ubiquitous in tabletop SDOCT systems and typically consists of a bank of LEDs or a screen to provide a target on which the patient can focus during imaging. Addition of an internal fixation target facilitates alignment in pediatric patients capable of fixation.

In some embodiments, a point-fixation target is provided in a simplified structure. It is important to maintain a central gaze, preferably with the subject eye focused at infinity, to capture quality images centered of the macula centered on the fovea. As shown in FIG. 5, a central fixation target 332 may be collocated in the aperture of the ring illuminator. Such a configuration has multiple benefits, including the elimination of a separate dichroic or additional optical paths elements.

For the illuminator system described, a 0.12 NA single mode fiber or ring of fibers, as shown in FIG. 10, recessed a distance of 6.6 mm 334 behind the illumination fiber ring. The illumination of the fixation fiber bundle can be sequenced to occur after the fundus image is taken so the corneal reflection will not affect the fundus image. The fundus camera and fixation fiber illumination are mutually exclusive. In this instance, the imaged spot diameter on the retina is approximately 175 um. A ring of fibers with an image diameter of approximately one half of a millimeter focused at infinity provides a comfortable central field fixation target for a patient.

Some aspects of the present invention may be implemented by a data processing system. Exemplary embodiments of a data processing system 1230 configured in accordance with embodiments of the present invention will be discussed with respect to FIG. 12. The data processing system 1230 may include a user interface 1244, including, for example, input device(s) such as a keyboard or keypad, a display, a speaker and/or microphone, and a memory 1236 that communicate with a processor 1238. The data processing system 1230 may further include I/O data port(s) 1246 that also communicates with the processor 1238. The I/O data ports 1246 can be used to transfer information between the data processing system 1230 and another computer system or a network using, for example, an Internet Protocol (IP) connection. These components may be conventional components such as those used in many conventional data processing systems, which may be configured to operate as described herein.

Figure 12:
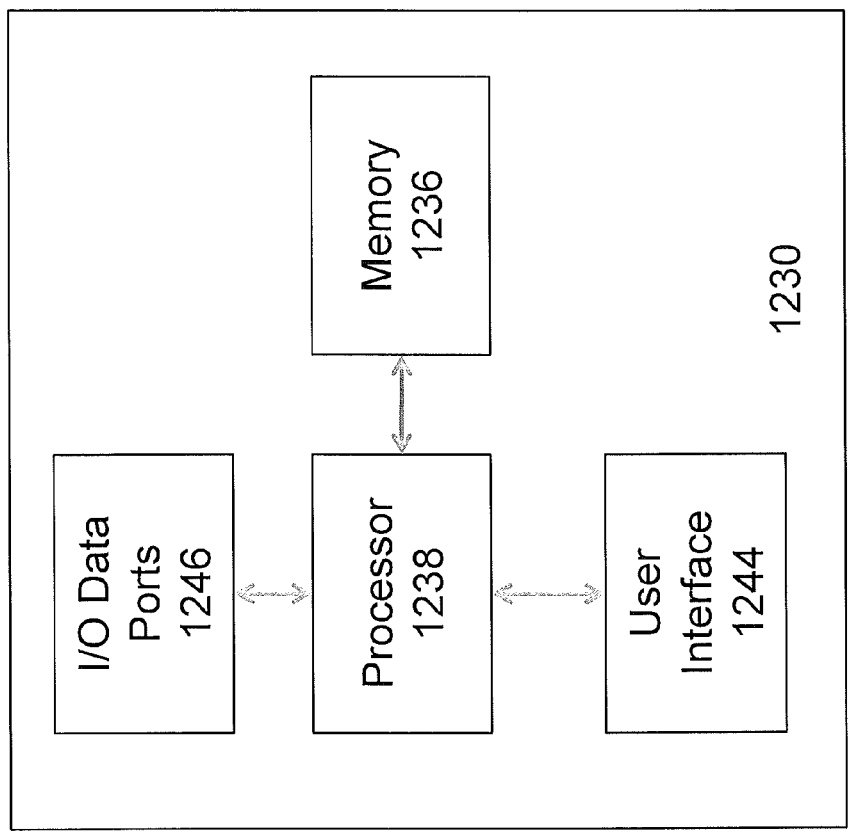
FIG. 12 is block diagram illustrating a data processing system configured in accordance with embodiments of the present inventive concept.
Figure 13:
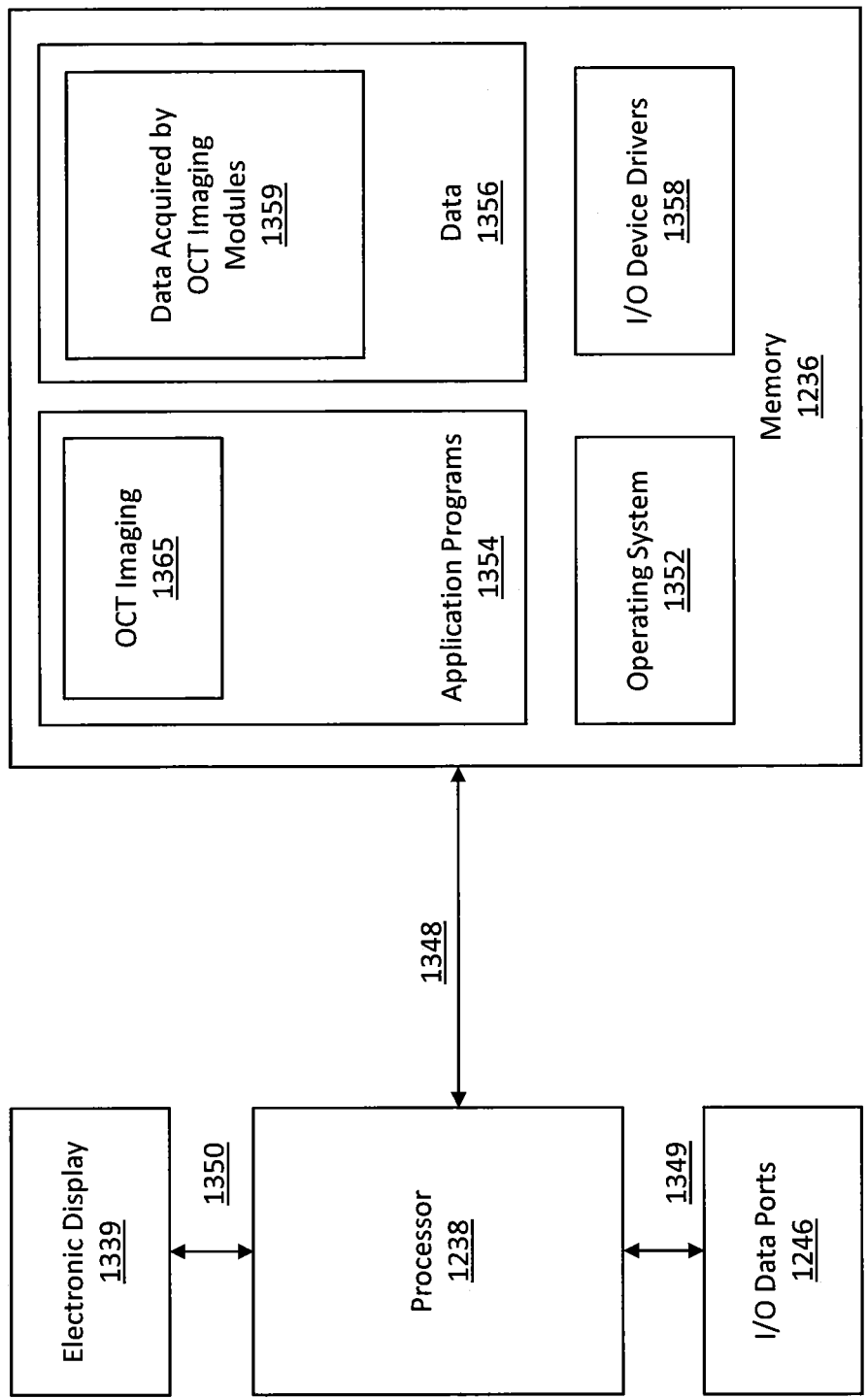
FIG. 13 is a more detailed block diagram of a data processing system of FIG. 12 in accordance with some embodiments of the present inventive concept.

Referring now to FIG. 13, a more detailed block diagram of a data processing system of FIG. 12 is provided that illustrates systems, methods, and computer program products in accordance with some embodiments of the present invention, which will now be discussed. As illustrated in FIG. 13, the processor 1238 communicates with the memory 1236 via an address/data bus 1348, the I/O data ports 1246 via address/data bus 1349 and the electronic display 1339 via address/data bus 1350. The processor 1238 can be any commercially available or custom enterprise, application, personal, pervasive and/or embedded microprocessor, microcontroller, digital signal processor or the like. The memory 1236 may include any memory device containing the software and data used to implement the functionality of the data processing system 1230. The memory 1236 can include, but is not limited to, the following types of devices: ROM, PROM, EPROM, EEPROM, flash memory, SRAM, and DRAM.

As further illustrated in FIG. 13, the memory 1236 may include several categories of software and data used in the system: an operating system 1352; application programs 1354; input/output (I/O) device drivers 1358; and data 1356. As will be appreciated by those of skill in the art, the operating system 1352 may be any operating system suitable for use with a data processing system, such as OS/2, AIX or zOS from International Business Machines Corporation, Armonk, N.Y., Windows95, Windows98, Windows2000 or WindowsXP, or Windows CE or Windows 7 from Microsoft Corporation, Redmond, Wash., Palm OS, Symbian OS, Cisco IOS, VxWorks, Unix or Linux. The I/O device drivers 1358 typically include software routines assessed through the operating system 1352 by the application programs 1354 to communicate with devices such as the I/O data port(s) 1246 and certain memory 1236 components. The application programs 1354 are illustrative of the programs that implement the various features of the some embodiments of the present invention and may include at least one application that supports operations according to embodiments of the present invention. Finally, as illustrated, the data 1356 may include data acquired using the OCT imaging module 1365, which may represent the static and dynamic data used by the application programs 1354, the operating system 1352, the I/O device drivers 1358, and other software programs that may reside in the memory 1236.

As further illustrated in FIG. 13, according to some embodiments of the present invention, the application programs 1354 include OCT imaging modules 1365. While the present invention is illustrated with reference to OCT imaging modules 1365 as being application programs in FIG. 13, as will be appreciated by those of skill in the art, other configurations fall within the scope of the present invention. For example, rather than being application programs 1354, these circuits and modules may also be incorporated into the operating system 1352 or other such logical division of the data processing system. Furthermore, while the OCT imaging modules 1365 are illustrated in a single system, as will be appreciated by those of skill in the art, such functionality may be distributed across one or more systems, Thus, the present invention should not be construed as limited to the configuration illustrated in FIG. 13, but may be provided by other arrangements and/or divisions of functions between data processing systems. For example, although FIG. 13 is illustrated as having various circuits, one or more of these circuits may be combined without departing from the scope of the present invention.

It will be understood that the OCT imaging modules 1365 may be used to implement various portions of the present invention capable of being performed by a data processing system. For example, the OCT imaging modules may be used to process and assess the images produced by the OCT system according to some embodiments of the present invention.

Example embodiments are described above with reference to block diagrams and/or flowchart illustrations of methods, devices, systems and/or computer program products. It is understood that a block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means (functionality) and/or structure for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the functions/acts specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, example embodiments may be implemented in hardware and/or in software (including firmware, resident software, micro-code, etc.). Furthermore, example embodiments may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Computer program code for carrying out operations of data processing systems discussed herein may be written in a high-level programming language, such as Java, AJAX (Asynchronous JavaScript), C, and/or C++, for development convenience. In addition, computer program code for carrying out operations of example embodiments may also be written in other programming languages, such as, but not limited to, interpreted languages. Some modules or routines may be written in assembly language or even micro-code to enhance performance and/or memory usage. However, embodiments are not limited to a particular programming language. It will be further appreciated that the functionality of any or all of the program modules may also be implemented using discrete hardware components, one or more application specific integrated circuits (ASICs), or a field programmable gate array (FPGA), or a programmed digital signal processor, a programmed logic controller (PLC), or microcontroller.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated.

In the drawings and specification, there have been disclosed exemplary embodiments of the invention. However, many variations and modifications can be made to these embodiments without substantially departing from the principles of the present invention. Accordingly, although specific terms are used, they are used in a generic and descriptive sense only and not for purposes of limitation, the scope of the invention being defined by the following claims.

That which is claimed is:

1. A system for imaging a subject, the system comprising:
two imaging paths, a scanning beam optical coherence tomography (OCT) imaging path and a video imaging path,
wherein the scanning beam OCT imaging path comprises:
a source of broadband optical radiation, a beamsplitter dividing the source of broadband optical radiation into a reference path and a sample path; and a beamsplitter that mixes source light reflected from the subject in the sample path with source light returned from a reference reflector in the reference path to create a wavelength dependent interferogram directed along a detection path to a detection module;

wherein the video imaging path comprises:
an illumination path including a source of optical radiation for illuminating the sample;
an image capture path including an image capture device for capturing an image of an illuminated region of the subject; and
a beam combiner for coupling the illumination path with the image capture path;

a dichroic beamsplitter configured to couple the scanning beam OCT imaging path and the video imaging path, wherein the scanning beam OCT imaging path and the video imaging path share a common objective lens;

wherein the scanning beam OCT imaging path and the video imaging path share a common intermediate conjugate image plane between the dichroic beamsplitter and the subject;

wherein focal control is achieved for the scanning beam OCT imaging path and the video imaging path concurrently through adjustment of one or more common optical elements distal to the common intermediate conjugate plane;

wherein the illuminator is a fiber ring illuminator;

wherein a ring of illumination for the fiber ring illuminator is coaxial with the scanning beam OCT imaging path over a region where the scanning beam OCT imaging path and the video imaging path are in common; and wherein the fiber ring illuminator comprises a ring of optical fibers that defines an annulus.

2. The system of Claim 1, wherein a radiant numerical aperture of the optical fibers in the annulus is between 0.16 and 0.28.

3. The system of claim 2:
wherein the system further comprises a lens following the fiber ring illuminator and preceding the beam combiner that couples the illumination path with the image capture path; and wherein an image of the ring illuminator is focused onto a vicinity of a pupil of an eye of the subject.

4. The system of claim 1, wherein the illumination path further comprises a fixation target.

5. The system of claim 4 wherein the fixation target comprises one or more single-mode optical fibers situated within an annular boundary of the ring illuminator, wherein end faces of optical fibers that comprise the fixation target are axially offset from end faces of the optical fibers that comprise the ring illuminator, such that an image of an end face of the one or more single mode fibers is confocal with an OCT scanning beam at the subject.

6. The system of claim 1, wherein the image device is configured to:
provide a real-time video image to aid alignment of an OCT beam;
capture a photographic reference image of a sample to use as a comparison to an OCT depth-resolved image;
enable full color or hyperspectral photography for emphasizing various features of an imaged structure and various depths of the image structure; and/or
enable fluorescent image photography for emphasizing various features of the imaged structure and various depths of the image structure.

7. The system of claim 1, wherein the illumination source includes optical radiation in a wavelength range of 650 to about 740 nm.

8. The system of Claim 7, wherein the illumination source comprises a light emitting diode (LED).

9. The system of Claim 1, wherein the dichrotic beamsplitter comprises a thin film filter.

10. The system of claim 1, wherein the system further includes a real-time range finder configured to guide a photographer to a correct working distance between the objective lens and the subject.

11. The system of claim 1, further comprising an electromechanical reference arm.

12. The system of claim 1, wherein the system is fitted within a compact housing, the housing including a cable tether to a remainder of the OCT system, the housing sized to provide a handheld system for imaging the subject.

* * * * *

UNITED STATES PATENT AND TRADEMARK OFFICE
CERTIFICATE OF CORRECTION

PATENT NO. : 8,896,842 B2  
APPLICATION NO. : 13/198117  
DATED : November 25, 2014  
INVENTOR(S) : Bower et al.

Page 1 of 1

It is certified that error appears in the above-identified patent and that said Letters Patent is hereby corrected as shown below:

In the Specification:
Column 13, Line 35: Please correct "with a 530+43 nm bandpass"
to read -- with a 530 ± 43 nm bandpass --

In the Claims:
Column 22, Lines 27 and 28: Please correct "range of 650 to about 740 nm."
to read -- range of 650 to 740nm. --

Signed and Sealed this
Twenty-first Day of April, 2015

Michelle K. Lee
*Director of the United States Patent and Trademark Office*